United States Patent [19]

Kappernaros

[11] Patent Number: 4,959,087
[45] Date of Patent: Sep. 25, 1990

[54] AIR CONDITIONING SYSTEM FILTER WITH VARIABLE RATE SCENT RELEASE

[76] Inventor: James Kappernaros, 1205 Powers Run Rd., Pittsburgh, Pa. 15237

[21] Appl. No.: 365,830

[22] Filed: Jun. 14, 1989

[51] Int. Cl.⁵ .................................................. A61L 9/04
[52] U.S. Cl. ........................................ 55/279; 55/511; 239/60; 422/120
[58] Field of Search ............... 55/279, 511, DIG. 31; 239/60; 422/4, 5, 120

[56] References Cited

U.S. PATENT DOCUMENTS

| | | | |
|---|---|---|---|
| 1,881,086 | 10/1932 | Marshall | 55/279 |
| 1,887,242 | 11/1932 | Martinson | 261/107 |
| 2,388,933 | 11/1945 | Pearson | 261/107 |
| 2,965,197 | 12/1960 | Dow et al. | 55/DIG. 31 |
| 3,230,033 | 1/1966 | Hamilton et al. | 422/121 |
| 3,274,758 | 9/1966 | Parman | 55/279 |
| 4,028,073 | 6/1977 | Swaim | 55/279 |
| 4,118,226 | 10/1978 | Bourassa | 55/279 |
| 4,159,672 | 7/1979 | Garquilo et al. | 98/30 |
| 4,464,187 | 8/1984 | Kershaw | 55/DIG. 31 |
| 4,465,232 | 8/1984 | Field | 239/60 |
| 4,563,333 | 1/1986 | Frigon | 55/279 |
| 4,604,114 | 8/1986 | Ward | 55/279 |
| 4,689,058 | 8/1987 | Vogt et al. | 55/279 |
| 4,875,912 | 10/1989 | Fulmer | 55/279 |

FOREIGN PATENT DOCUMENTS 533339  2/1941  United Kingdom ............... 55/279

*Primary Examiner*—Jay H. Woo
*Assistant Examiner*—C. Scott Bushey
*Attorney, Agent, or Firm*—Fleit, Jacobson, Cohn, Price, Holman & Stern

[57] ABSTRACT

A forced air handling system filter is provided including an inwardly opening, channel-shaped peripheral frame from which corresponding peripheral portions of a panel-like filter batt is supported and an elongated bar of scented material is provided and stationarily supported within a pocket of the frame opening inwardly of the inner periphery thereof. The bar includes a scent impervious cover completely enclosing the bar and one longitudinal edge of the bar projects outwardly of the aforementioned pocket toward the remote side of the frame and that portion of the cover disposed over the bar marginal portion includes a tear strip extending longitudinally thereof. The tear strip is adjustably tearable from the remainder of the cover to expose a corresponding portion of the bar for scent release therefrom.

11 Claims, 1 Drawing Sheet

AIR CONDITIONING SYSTEM FILTER WITH VARIABLE RATE SCENT RELEASE

BACKGROUND OF THE INVENTION

1. Field of the Invention

This invention relates generally to a panel-type air filter including structure whereby a scent may be introduced into air flowing through the filter at an adjustable rate generally proportional to the flow rate of air through the filter. The filter has been designed primarily for use in residential forced air heating and air conditioning systems, but also may be used in domestic range hoods as well as other air handling systems incorporating an air filter and which may benefit from a reasonably controlled rate of scent release into the air passing through the air filter.

2. Description of Related Art

Various different forms of scent releasing structure heretofore has been provided for releasing scent into air passing through a forced air handling system. Examples of these previously known structures are disclosed in U.S. Pat. Nos. 1,887,242, 2,965,197, 3,230,033 and 4,159,672. In addition U.S. Pat. No. 2,388,933 discloses structure by which a matt-type filter panel may be wetted with a liquid such as oil.

However, the above mentioned prior patents do not disclose a structure and method by which a variable rate scent discharge element may be added to a conventional air filter panel such as that disclosed in U.S. Pat. No. 2,965,197 during the manufacture of the filter panel (or after purchase thereof) and at a cost only slightly greater than the cost of the conventional air filter panel plus the cost of the scent discharge element.

SUMMARY OF THE INVENTION

The filter and scent discharging element combination of the instant invention utilizes a substantially conventional rectangular panel-like filter including a peripheral frame incorporating peripheral sides which are U-shaped in cross section and of the frame opening inwardly and a panel-like batt of filter material having its marginal edges received and supported between the opposing leg portions of the rectangular frame sides. In addition, a bar-type scent discharge element is frictionally gripped and glued between one of the legs of the filter frame and the opposing side of the panel-like batt of the air filter.

The main object of this invention is to provide a panel-like air filter for use in hot air heating systems and air conditioning systems and which incorporates an adjustably variable scent release structure whereby air passing through the air filter will be scented. It is also envisioned that the scent releasing element further may include an air purification agent.

Another object of this invention is to provide a scent release air filter which may be used as a substantially exact replacement for conventional panel-type air filters presently utilized in domestic and business forced hot air and air conditioning systems.

Another very important object of this invention is to provide an air filter including variable rate scent discharge means and wherein the air filter may be marketed with the scent discharge means thereof enclosed within an openable air impermeable cover.

A further object of this invention is to provide an air filter in accordance with the preceding objects and including scent discharge means which may be operative to release a scent into the air passing through the air filter throughout substantially the full air filtering life of the filter up until the air filter itself needs to be replaced.

Another very important object of this invention is to provide an air filter having scent discharge means operatively associated therewith and with the scent discharge means requiring no maintenance throughout the effective operating life of the associated air filter.

A final object of this invention to be specifically enumerated herein is to provide an air filter with variable rate scent release and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
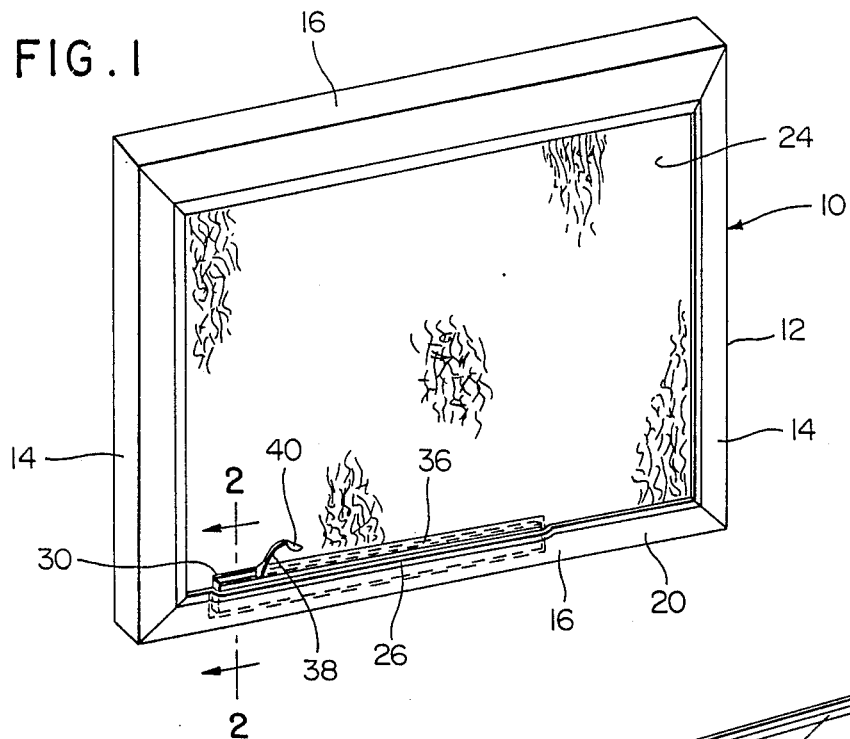
FIG. 1 is a perspective view of a substantially conventional low cost furnace-air conditioning system air filter incorporating a variable discharge scent release element in accordance with the present invention.
Figure 3:
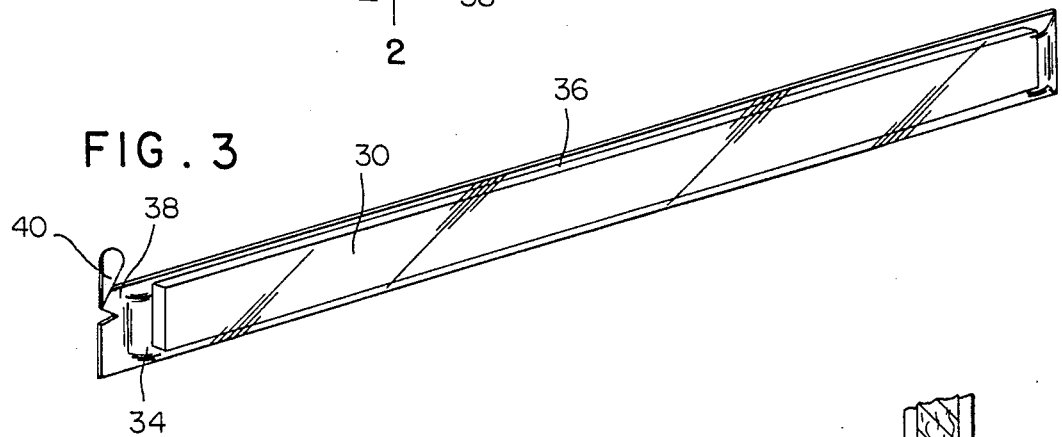
FIG. 3 is a perspective view of the variable rate scent discharge element of the instant invention.
Figure 2:
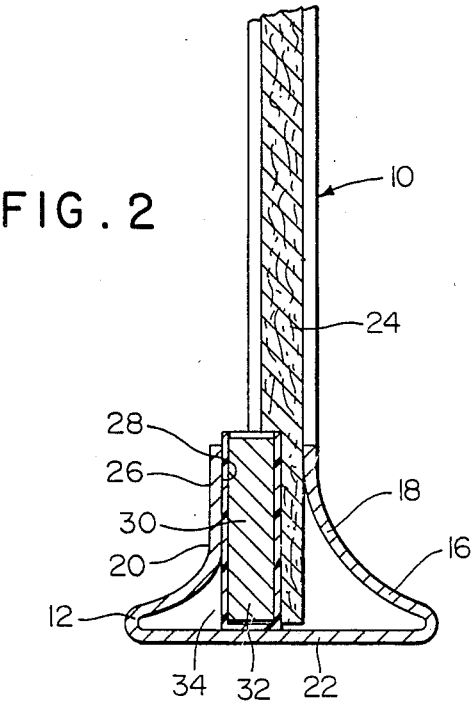
FIG. 2 is an enlarged fragmentary vertical sectional view taken substantially upon the plane indicated by the section line 2—2 of FIG. 1.

Referring now more specifically to the drawings, the numeral 10 generally designates a substantially conventional hot air furnace-air conditioning filter of the type disclosed in U.S. Pat. No. 2,965,197. The air filter 10 includes a frame 12 of generally rectangular configuration. The frame 12 includes two pairs of parallel opposite sides 14 and 16 and each side 14, 16 is constructed of stiff paper and is generally U-shaped in cross section including a pair of opposite side flanges or legs 18 and 20 interconnected along corresponding longitudinal margins by an outer wall or bight portion 22. The longitudinal margins of the opposite side flanges 18 and 20 between which the bight portion 22 extends are spaced a predetermined distance apart and the inner longitudinal marginal edges of the flanges 18 and 20 remote from the bight portion 22 are spaced closer together and clampingly engage therebetween corresponding marginal edges of a batt-type filter panel 24.

One end portion 26 of the flange 20 of the lower side 16 of the frame 12 illustrated in FIG. 1 is laterally outwardly offset relative to the remainder of that flange 20 in order to define an elongated pocket 28 in which to receive an elongated bar 30 of scent release material 32 between the end portion 26 and the opposing surface of the filter panel 24. The bar 30 is rectangular in cross sectional shape with its major axis generally paralleling the plane of the frame 12 and the bar 30 is covered by a scent impermeable cover 34. Further, that portion 36 of the cover 34 disposed about the terminus of the transverse major axis of the bar 32 facing inwardly of the frame 12 includes a tear strip 38 having a free pull tab 40 anchored to one end thereof and the pull tab 40 may be grasped and pulled inwardly of the frame 12 to variably tear the tear strip 38 from the remainder of the cover 34.

Tearing only a small length of the tear strip 38 from the remainder of the cover 34 will expose only a small portion of the scent release material 32 comprising the bar 30 and, accordingly, the scent discharge from the bar 30 will be at a slow rate. If, on the other hand, a greater length portion of the tear strip 38 is torn from the remainder of the cover 34, the release of scent from the scent release material 32 will be lower at a greater rate.

It is also to be noted that scent release from the scent release material 32 will be at a considerably retarded rate when air is not flowing through the filter 12 as opposed to the scent release rate that occurs when air is flowing through the filter 12. Therefore, should the associated forced air furnace or air conditioning system not be in operation, the release of scent from the scent release material 32 will be very low. On the other hand, when a force air furnace or air conditioning system is in operation, the release of scent from the scent release material will be accelerated and determined to a great degree by the amount the tear strip 38 is torn from the remainder of the cover 34.

When the frame 18 is constructed of stiff paper, the marginal edges of the flanges 18 and 20 remote from the bight portion 22 are secured relative to each other by a bonding agent (not shown) therebetween passing through the interstices of the filter panel 24. However, if the frame 18 is constructed of a more rigid material such as plastic or metal, the outer marginal edges of the filter panel 24 are merely received between the opposite side flanges 18 and 20 of the frame 12.

It is to be noted, however, that the addition of the bar 30 to the frame 12 will not increase the total width of the frame 18 defined by the maximum width of the bight portions 22 thereof. In this manner, the air filter 10, including the bar 30, may be used as a full replacement for a conventional air filter not equipped with the bar 30.

It is also pointed out that the bar 30 may be marketed separately and that either flange 18 or 20 may have an appropriate length portion thereof pried loose from the bonding material (not shown) bonding the inner marginal edge portions of the flanges 18 and 20 together through the filter panel or batt 24 and the bar 30 may be inserted into the pocket 28 thus formed. Still further, the bar 30 easily may be inserted between the filter panel or batt 24 and one of the flanges of a plastic or metal frame. Of course, if the filter 10 is disposed upright in the manner illustrated in FIG. 1 the bar 28 will be placed along the lower side 16 of the frame 12.

Further, the length of the bar and scent release rate of the material 32, in conjunction with a predetermined amount the tear strip 38 is torn from the remainder of the cover 34, may indicate, when scent is no longer being released, the time to replace the air filter in order to maintain optimum air filtering capacity.

The foregoing is considered as illustrative only of the principles of the invention Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. An air filter including a generally rectangular, panel-like batt of filter material supported from a surrounding rectangular frame incorporating four sides, each of said sides being generally U-shaped in cross section including a pair of opposite side elongated flanges extending therealong and interconnected along one pair of corresponding longitudinal margins by a bight portion extending therebetween with said frame sides opening inwardly of the periphery of said frame and each frame side receiving the corresponding marginal edge of said batt between the opposing surfaces of the other pair of longitudinal margins of the opposite side flanges thereof, an elongated scented material bar extending longitudinally along one of said frame sides and stationarily supported between one of said side flanges of said one frame side and the opposing marginal edge portion of said batt with a major portion of said bar disposed between said side flanges of said one frame side, said scented bar including at least one exposed surface thereof facing outwardly from between said side flanges inwardly of said frame.

2. The air filter of claim 1 wherein said opposing surfaces, other than those portions thereof between which said bar is disposed, tightly clamp the corresponding marginal edge of said batt therebetween.

3. The air filter of claim 2 wherein said opposing surfaces are adhered together by bonding material disposed therebetween extending through the interstices of said batt.

4. The air filter of claim 1 wherein said bar is generally rectangular in cross sectional shape and is positioned relative to said frame with one terminus of the major cross sectional axis thereof facing inwardly of said one frame side.

5. The air filter of claim 4 wherein said bar includes a scent impermeable cover disposed thereover, a longitudinal extent of said cover disposed over said one terminus of said major transverse axis of said bar including a tear strip extending therealong, said tear strip being selectively tearable from the remainder of said cover for variably exposing said bar.

6. The air filter of claim 5 wherein said opposing surfaces, other than those portions thereof between which said bar is disposed, tightly clamp the corresponding marginal edge of said batt therebetween.

7. The air filter of claim 6 wherein said opposing surfaces are adhered together by bonding material disposed therebetween extending through the interstices of said batt.

8. In combination with an air filter of the type including a panel-like batt of air filtering material and an open frame extending about the periphery of said panel-like batt for support of the periphery of said batt from said frame, said frame including one marginal portion thereof defining an elongated pocket extending along and opening inwardly of said one marginal portion of said frame across said panel-like batt toward an opposite marginal portion of said frame, an elongated scented material bar stationarily supported in said pocket, said scented material bar including at least an exposed surface thereof facing outwardly of said pocket.

9. The air filter of claim 8 wherein said bar is generally rectangular in cross sectional shape and is positioned relative to said frame with the terminus of the major cross sectional axis thereof facing inwardly of said one frame side.

10. The air filter of claim 9 wherein said bar includes a scent impermeable cover disposed there over, a longitudinal extend of said cover disposed over said one terminus of said major transverse of said bar including a tear strip extending therealong selectively tearable from the remainder of said cover for variably exposing said bar.

11. The air filter of claim 9 wherein said bar includes a predetermined rate of scent release such that after operational usage of the air filter for a predetermined time the bar will no longer be capable of releasing scent, the absence of scent in the air filtered by the air filter being indicative of the need to replace the air filter to maintain optimum air filtering capacity of the corresponding air handling system.

* * * * *